United States Patent [19]
Baldwin

[11] 4,000,282
[45] Dec. 28, 1976

[54] 2-(3-TERT. BUTYL OR ISOPROPYLAMINO-2-HYDROXYPROPOXY)-3-CYANOPYRIDINES
[75] Inventor: John J. Baldwin, Lansdale, Pa.
[73] Assignee: Merck & Co., Inc., Rahway, N.J.
[22] Filed: Dec. 16, 1974
[21] Appl. No.: 533,385
[52] U.S. Cl. .................. 424/263; 260/294.8 R; 260/294.9
[51] Int. Cl.$^2$ ...................... C07D 213/85
[58] Field of Search ............ 260/294.9; 424/263
[56] References Cited
UNITED STATES PATENTS
3,459,782  8/1967  Koppe et al. ............ 260/465
FOREIGN PATENTS OR APPLICATIONS
2,406,930  8/1974  Germany ............ 260/294.9
1,305,644  2/1973  United Kingdom OTHER PUBLICATIONS
Meyer et al. "J. Med. Chem." Vol. 16 (1973) pp. 1113-1114.
Grenwich et al. "J. Med. Chem." Vol. 15 (1972) p. 1321.

Primary Examiner—Henry R. Jiles
Assistant Examiner—R. W. Ramsuer
Attorney, Agent, or Firm—J. Jerome Behan; Daniel T. Szura

[57] ABSTRACT

Novel 2-(3-tert. butyl or isopropylamino-2-hydroxypropoxy)-3-cyanopyridines, their pharmaceutically their preparation are disclosed. These pyridines are vasodilators having anti-hypertensive activity of rapid onset and extended duration and reduced tendency to cause undesirable tachychardia; they are also β-adrenergic blocking agents.

9 Claims, No Drawings

2-(3-TERT. BUTYL OR ISOPROPYLAMINO-2-HYDROXYPROPOXY)-3-CYANOPYRIDINES

BACKGROUND OF THE INVENTION

The present invention concerns 2-substituted aminohydroxypropoxy-3-cyanopyridines which have antihypertensive activity of rapid onset and extended duration and are β-adrenergic blocking agents.

Hypertension in man and other animals can be treated with various chemical agents. One such class of agents is that known as the β-adrenergic blocking agents or β-blockers. While this class of agents can have antihypertensive activity, the onset of this activity is generally gradual. The structure and activity of β-blockers is generally discussed in "Clinical Pharmacology and Therapeutics" 10, 252,306 (1969). Cyano substituted carbocyclic and heterocyclic aryl β-adrenergic blocking agents are disclosed in Belgian Pat. No. 707,050 and Netherlands Pat. No. 69.07700. Cyano substituted heteroaryl β-adrenergic blocking agents are also disclosed in German Pat. No. 2,406,930.

Another class of antihypertensive agents are the vasodilators. Vasodilators, however, normally cause undesirable tachychardia.

Novel 2-(3-C$_3$-C$_4$-branchedalkylamino-2-hydroxypropoxy)-3-cyanopyridines have been discovered. These compounds are vasodilators having antihypertensive activity of rapid onset and extended duration and a reduced tendency to cause undesirable tachychardia — and they are β-adrenergic blocking agents.

SUMMARY OF THE INVENTION

Novel 2-(3-tert. butyl or isopropylamino-2-hydroxypropoxy)-3-cyanopyridines and their pharmaceutically acceptable salts which are vasodilators having rapid and lasting antihypertensive effect and a reduced tendency to cause tachychardia and are also β-adrenergic blocking agents.

DESCRIPTION OF THE PREFERRED EMBODIMENTS

An embodiment of the present invention is compounds having the formula

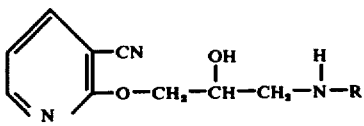

wherein R is isopropyl or tert. butyl, and pharmaceutically acceptable salts thereof. A preferred substituted pyridine is 2-(3-tert. butyl-2-hydroxypropoxy)-3-cyanopyridine and its pharmaceutically acceptable salts.

The substituted pyridines of the present invention include all the optical isomer forms, that is mixtures of enantiomers e.g. racemates as well as the individual enantiomers. These individual enantiomers are commonly designated according to the optical rotation they effect, by (+) and (−), (L) and (D), (l) and (d) or combinations of these symbols. The symbols (S) and (R) stand for sinister and rectus respectively and designate an absolute spatial configuration of the enantiomer.

The pyridines of the present invention can be prepared by any convenient process.

One such process involves the coupling of a 2-halo-3-cyanopyridine with a suitable substituted oxazolidine and hydrolysing the reaction product obtained. This process is illustrated by the following set of reaction equations:

REACTION A

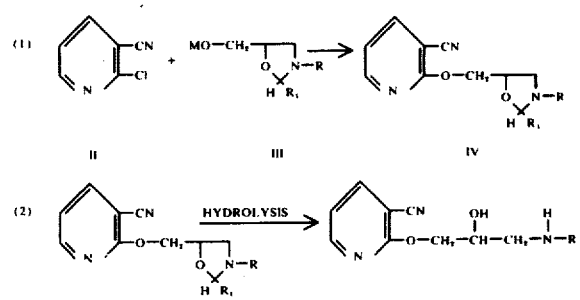

R in the above equations is tert. butyl or isopropyl. M is an alkali metal, either potassium or sodium. R$_1$ can be hydrogen or the residue of any suitable aldehyde

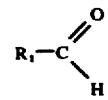

e.g. arylaldehyde, such as benzaldehyde, naphthaldehyde and the like, or alkanal such as acetaldehyde, butyraldehyde and the like. The process for preparing oxazolidines where M is hydrogen is disclosed in U.S. Pat. No. 3,718,647 and U.S. Pat. No. 3,657,237 and to the extent necessary the pertinent disclosure is incorporated herein by reference. The alkali metal salt of the oxazolidine is prepared in a conventional manner by reaction of the corresponding hydroxymethyl oxazolidine with an appropriate amount of base such as potassium hydroxide, sodium hydroxide, sodium methoxide and the like. However, this Reaction A may also be carried out with in-situ formation of the alkali metal oxazolidine salt of Formula IV by reacting the oxazolidine

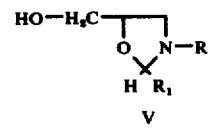

with the Formula II pyridine in the presence of a strong base such as an alkali metal alkoxide (e.g. K—O—C—(CH$_3$)$_3$) or hydroxide (e.g. NaOH) or sodium hydride.

The coupling reaction can be carried out at temperatures ranging from about 0° to about 100° C. A temperature range of about 10° to about 50° C is preferred. The reaction is generally carried out in a solvent. Any suitable solvent may be used. Examples of useful solvents are dimethylformamide, dimethylsulfoxide, hexamethylphosphoramide, $C_1$–$C_6$ alkanols and the like. The hydrolysis is carried out using conventional acid hydrolysis reagents and techniques e.g. treatment with a solution of any strong mineral acid such as HCl or $H_2SO_4$.

The coupling reaction is ordinarily carried out at atmospheric pressure. Higher pressures may be used if desired.

When the racemic oxazolidine (Formula III or V) is used as a reactant, the Formula I product is obtained as a racemate. The racemate may be separated into its individual enantiomers by conventional resolution techniques.

By using a single optical isomer of the Formula IV or V oxazolidine in the above reactions, the Formula I product may be obtained directly as a single enantiomer. Thus, if the S-isomer of the oxazolidine is used, then the product obtained will be the S-isomer. This provides a convenient way for directly preparing individual isomers of the present pyridines.

The compounds of the present invention also include the pharmaceutically acceptable salts of the novel pyridines. These salts are generally salts of the Formula I pyridines and organic or inorganic acids. These salts are prepared by treating the pyridine with an appropriate amount of a useful acid, generally in a suitable solvent. Examples of useful organic acids are carboxylic acids such as maleic acid, acetic acid, tartaric acid, propionic acid, fumaric acid, isethionic acid, succinic acid, pamoic acid, oxalic acid and the like; useful inorganic acids are hydrohalo acids such as HCl, HBr, HI; sulfuric acid, phosphoric acid and the like.

The compounds of the present invention have a dual action. They are (1) vasodilators having antihypertensive activity of rapid onset and extended duration and reduced tendency to cause undesirable tachychardia and (2) β-adrenergic blocking agents. This antihypertensive activity is believed to be the result of peripheral vasodilation via a mechanism not directly related to β-adrenergic blockade. Thus, the present pyridines provide (a) an advantage over ordinary vasodilators since vasodilator treatment normally results in an undesirable tachychardia response and (b) an advantage over the ordinary β-adrenergic blocking agent by having an immediate and substantial antihypertensive effect.

This rapid onset antihypertensive activity is determined by administering (orally) a representative pyridine of Formula I to spontaneously hypertensive (SH) rats and measuring the effect on blood pressure. A representative substituted pyridine, (S)-2-(3-tert.butylamino-2-hydroxypropoxy)-3-cyanopyridine hydrochloride, was found to rapidly lower the SH rat's blood pressure.

The β-adrenergic blocking activity of the present pyridines is determined by measuring the ability of a representative pyridine to block isoproterenol induced β-adrenergic stimulant effects such as heart rate increase, hypotension and bronchodilatation, in animals. A representative pyridine, (S)-2-(3-tert.- butylamino-2-hydroxypropoxy)-cyanopyridine hydrochloride, was administered intravenously and found to behave as a β-adrenergic blocking agent by this protocol.

The ability of the present pyridine to reduce blood pressure, in an SH rat, rapidly and for extended duration, indicates that the present pyridines and their salts are useful to treat hypertension in humans. Likewise, the observed β-adrenergic blocking activity of these pyridines indicates that they are useful in humans as β-adrenergic blocking agents.

For use as antihypertensives and/or β-adrenergic blocking agents, the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like - or dissolved, dispersed or emulsified in a suitable liquid carrier - or in capsules or encapsulated in a suitable encapsulating material; or (2) for parenteral administration, dissolved, dispersed, or emulsified in a suitable liquid carrier or diluent or (3) as an aerosol or (4) as a suppository. The ratio of active ingredient (present compound) to compounding ingredients will vary as the dosage form requires.

The dosage level for the present compounds may be varied from about 0.01 mg. to about 50 mg. per kilogram of animal body weight per day. Daily doses ranging from about 0.04 to about 2.5 mg/kg are preferred, with about 0.08 to about 1.25 mg/kg being a more preferred range. Oral administration is preferred. Either single or multiple daily doses may be administered depending on unit dosage.

Following are examples illustrating pharmaceutical formulations containing the pyridines of the present invention. Conventional procedures are used for preparing these formulations.

| TABLET FORMULATION | |
|---|---|
| INGREDIENT | AMOUNT (Mg.) |
| 2-(3-isopropylamino-2-hydroxypropoxy)-3-cyanopyridine hydrogen maleate | 5.0 |
| calcium phosphate | 120.0 |
| lactose | 50.0 |
| starch | 23.5 |
| magnesium stearate | 1.5 |
| CAPSULE FORMULATION | |
| INGREDIENT | AMOUNT (Mg.) |
| (R)-2-(3-t-butylamino-2-hydroxypropoxy) 3-cyanopyridine | 5 |
| magnesium stearate | 2.0 |
| lactose, U.S.P. | 19.3 |
| INJECTABLE SOLUTION | |
| INGREDIENT | AMOUNT (Mg.) |
| 2-(3-t-butylamino-2-hydroxypropoxy)-3-cyanopyridine | 1 |
| sodium chloride | 9 |
| distilled water, q.s. 1.0 ml. | |
| LIQUID SUSPENSION | |
| INGREDIENT | AMOUNT (g/l) |
| (S)-2-(3-isopropylamino-2-hydroxypropoxy-3-cyanopyridine hydrochloride | 5.0 |
| Veegum H.V. | 3.0 |
| methyl paraben | 1.0 |
| kaolin | 10.0 |
| glycerin | 250.0 |
| water, q.s. ⟶ 1 liter | |

The following examples illustrate preparation of a representative pyridine of Formula I. All parts and percentages are by weight unless otherwise indicated.

EXAMPLE 1

(S)-2-(3-tert. butylamino-2-hydroxypropoxy)-3-cyanopyridine hydrochloride

To (S)-2-phenyl-3-tert. butyl-5-hydroxymethyloxazolidine (7 grams, 0.03 moles) in 35 ml. of N,N-dimethylformamide (DMF) is added 1.3 grams (0.03 moles of sodium hydride (57% dispersion in mineral oil). This mixture is heated 5 minutes over steam and then is allowed to stir 15 minutes at room temperature. 4.1 grams (0.03 moles) of 2-chloro-3-cyanopyridine in 20 ml of DMF is then added and the resultant reaction mixture is stirred four hours at room temperature. Water is then added and an oil separates. This oil is extracted three times with 25 ml of chloroform each time. This chloroform extract is dried over sodium sulfate and concentrated under reduced pressure (20 mm) over steam to yield the product, (S)-2-phenyl-3-tert. butyl-5-(3-cyano-2-pyridyloxymethyl)oxazolidine, as an oil. This oil is then suspended in 1N HCl (50 ml), heated 5 minutes over steam and then is stirred for 15 minutes at room temperature. The solution obtained is then extracted twice with 25 ml of diethylether each time. The extracted aqueous layer is made basic by addition of saturated aqueous sodium carbonate solution. This aqueous solution is then extracted with ethyl acetate (3 × 25 ml) and the ethylacetate solution is dried over sodium sulfate. The dried ethyl acetate solution is then concentrated under reduced pressure (20 mm) over steam to yield an oil. This oil is chromatographed on alumina. The chromatographic fractions are concentrated to yield an oil which is dissolved in diethyl ether. Ethanolic HCl (saturated solution) is added to this ether solution until solid separation is substantially complete. The separated semi-solid is recrystallized from isopropanol/ether (ether added to isopropanol to the point of turbidity) to yield 1 gram of (S)-2-(3-tert-butylamino-2-hydroxypropoxy)-3-cyanopyridine hydrochloride, melting at 161°–163° C.

While in Example 1 the S-isomer of the pyridine salt is prepared, the racemate is prepared by using racemic (S/R) oxazolidine reactant; the R-isomer is prepared by using R-oxazolidine reactant.

The free amine is obtained from the Example 1 salt by any conventional procedure e.g. by treating the salt with a base (e.g. NaOH) in solution and extracting the free amine therefrom.

Using the procedure of Example 1, (S)-2-(3-isopropylamino-2-hydroxypropoxy)-3-cyanopyridine hydrochloride is prepared by using the corresponding N-isopropyl oxazolidine in place of the N-tert. butyl oxazolidine.

Claims to the invention follow.

What is claimed is:

1. Compounds having the formula

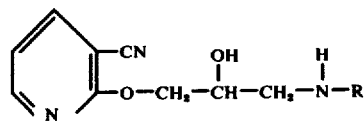

wherein R is isopropyl or tert. butyl, and pharmaceutically acceptable salts thereof.

2. Compounds of claim 1 wherein R is isopropyl.
3. Compounds of claim 1 wherein R is tert. butyl.
4. Compounds of claim 3 wherein said compounds are racemates.
5. Compounds of claim 3 wherein said compounds are in the rectus configuration.
6. Compounds of claim 3 wherein said compounds are in the sinister configuration.
7. The sinister form of 2-(3-tert. butylamino-2-hydroxypropoxy)-3-cyanopyridine and the hydrochloride salt thereof.
8. Pharmaceutical composition comprising an antihypertensive amount of compound of claim 1 in combination with an acceptable pharmaceutical carrier.
9. Method of reducing blood pressure in hypertensive animals which comprises administering to said animals an effective amount of compound of claim 1.

* * * * *